United States Patent

Sasaki et al.

[11] 4,261,989
[45] Apr. 14, 1981

[54] GELDANAMYCIN DERIVATIVES AND ANTITUMOR DRUG

[75] Inventors: Kazuya Sasaki; Yukio Inoue, both of Tokyo, Japan

[73] Assignee: Kaken Chemical Co. Ltd., Tokyo, Japan

[21] Appl. No.: 109,314

[22] Filed: Jan. 3, 1980

[30] Foreign Application Priority Data

Feb. 19, 1979 [JP] Japan .................. 54/17218

[51] Int. Cl.³ .................. A61K 31/395; C07D 225/06
[52] U.S. Cl. .................. 424/244; 424/263; 424/267; 424/274; 424/248.54; 260/239.3 B; 260/239.3 T; 260/239 BB
[58] Field of Search .................. 260/239.3 B, 239.3 T, 260/239 BB; 424/244, 263, 267, 248.54, 274

[56] References Cited

U.S. PATENT DOCUMENTS 3,987,035 10/1976 Rinehart et al. .............. 260/239.3 B Primary Examiner—Henry R. Jiles
Assistant Examiner—Robert T. Bond
Attorney, Agent, or Firm—Oblon, Fisher, Spivak, McClelland & Maier

[57] ABSTRACT

Geldanamycin derivatives the following formula

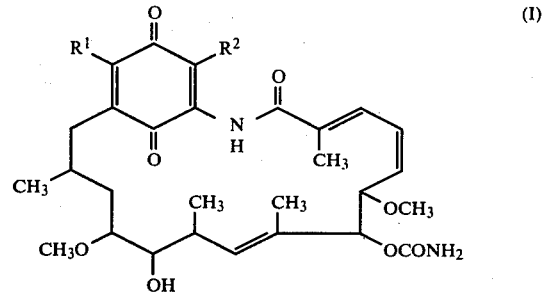

(I)

wherein $R^1$ represents a saturated alkylamino which should have at least two carbon atoms, an unsaturated alkylamino, a substituted lower alkylamino, cycloalkylamino, pyrrolidino or aralkylamino group or methoxy group; $R^2$ represents hydrogen atom, a halogen atom or a lower mono or dialkylamino; when $R^1$ is methoxy group, $R^2$ is a halogen atom or lower alkylamino group, or

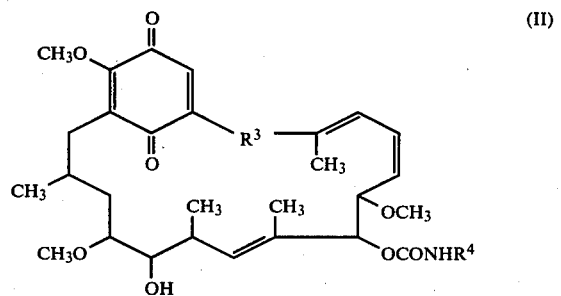

(II)

and Geldanamycin derivative is 8,9-epoxy-Geldanamycin.

The compounds are effective as antitumor drugs.

14 Claims, No Drawings

GELDANAMYCIN DERIVATIVES AND ANTITUMOR DRUG

BACKGROUND OF THE INVENTION

1. Field of the Invention

The present invention relates to novel Geldanamycin derivatives and antitumor drug containing the same as an active ingredient.

2. Description of the Prior Arts

Geldanamycin is the antiprotozoan antibiotic produced by streptomyces hygroscopicus var. geldanus var. nova strain (*Journal of Antibiotics* Vol. 23, Page 442 (1970)) and has the following formula

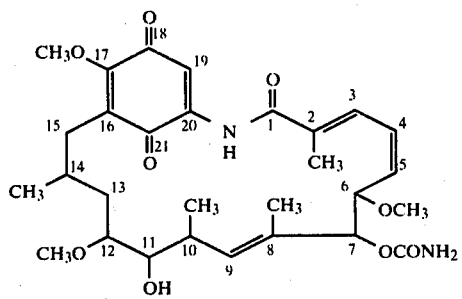

(*Journal of the American Chemical Society* Vol. 92, Page 7591 (1970)).

SUMMARY OF THE INVENTION

It is an object of the present invention to provide novel antitumor drugs.

The novel Geldanamycin derivatives of the present invention have the following formula

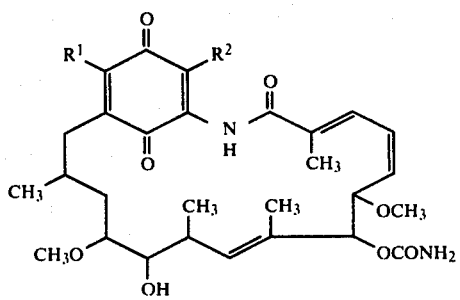
(I)

wherein $R^1$ represents a saturated alkylamino which should have at least two carbon atoms, an unsaturated alkylamino, a substituted lower alkylamino, cycloalkylamino, pyrrolidino or aralkylamino group or methoxy group; $R^2$ represents hydrogen atom, a halogen atom or a lower alkylamino group; when $R^1$ is methoxy group, $R^2$ is a halogen atom or a lower alkylamino group, or

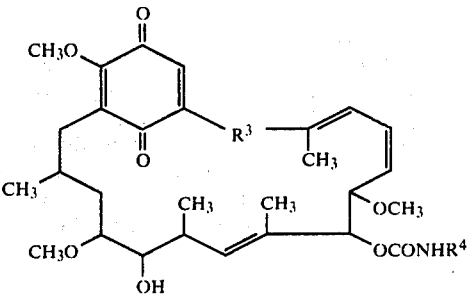
(II)

wherein $R^3$ represents

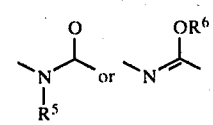

$R^4$, $R^5$ and $R^6$ respectively represent hydrogen atom or methyl group and at least one of $R^4$, $R^5$ and $R^6$ is methyl group; or

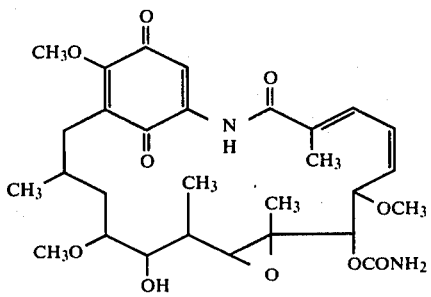
(III)

In the formula (I), when $R^1$ is methoxy group, $R^2$ is a halogen atom or a mono- or di-lower alkylamino group.

DETAILED DESCRIPTION OF THE PREFERRED EMBODIMENTS

The Geldanamycin derivatives having the formula (I) can be produced by reacting Geldanamycin with an amine having the formula

(IV)

wherein $R^7$ and $R^8$ respectively represent hydrogen atom or a saturated alkyl group having at least two carbon atoms; an unsaturated alkyl group, a substituted lower alkyl group a cycloalkyl group or an aralkyl group and both $R^7$ and $R^8$ can not be hydrogen atom and $R^7$ and $R^8$ can bonded to form one alkylene group.

The typical groups as $R^7$ or $R^8$ include ethyl, propyl, butyl, pentyl, hexcyl, heptyl, octyl, decyl, dodecyl, allyl or substituted lower alkyl groups (substituted with hydroxy, amino, methylamino, pyrrolidino, pyridinyl, alkoxy, piperadino, morpholino, cycloalkyl or hydroxyalkoxy group or a halogen atom); or cyclopropyl, cyclopentyl, cyclohexyl, cycloheptyl, cyclooctyl, benzyl, phenethyl group. The bonded $R^7$ and $R^8$ can be ethylene, tetramethylene, pentamethylene or hexamethylene group.

The typical amines include ethylamine, propylamine, butylamine, pentylamine, hexylamine, heptylamine, octylamine, decylamine, dodecylamine, allylamine, β-hydroxyethylamine, β-chloroethylamine, β-glycoxyethylamine, aminobutylamine, adamanthylmethylamine, cyclopropylamine, cyclopentylamine, cyclohexylamine, cycloheptylamine, benzylamine, phenethylamine, ethyleneimine, pyrrolidine, piperidine, dimethylamine, aminoethylamine, β-hydroxyethylamine, diglycolamine, β-morpholinoethylamine, β-piperadinoethylamine, 2'-, or 3'-, or 4'-picolylamine, β-pyrrolidinoethylamine, 2'-pyridinylethylamine, β-methoxyethylamine, β-N-methylaminoethylamine, etc. Methylamine can be used in the special condition.

The reaction of Geldanamycin with an amine can be carried out in the presence of an organic solvent.

Suitable organic solvents include alcohols, chlorinated hydrocarbons especially chloroform, dichloroethane, methanol etc. The solvent can be a mixture of two or more solvents. The components used in the reaction can be combined at a desired ratio such as an equimolar ratio or excess. It is preferable to use 1 to 50 mole equivalent of the amine per mole of Geldanamycin. The reaction is usually carried out at room temperature for 1 to 48 hours.

When excess of the amine is used in severe condition, both $R^1$ and $R^2$ are partially converted into the corresponding amino groups.

When excess of the di-lower alkylamine is used in the reaction, both $R^1$ and $R^2$ are partially converted into the corresponding dialkylamino groups, though $R^1$ is partially remained as methoxy group.

The Geldanamycin derivatives having the formula (I) wherein $R^1$ is methoxy group and $R^2$ is a halogen atom, such as Br, I, Cl or F, espcially Br, I or Cl can be obtained by a halogenation of Geldanamycin. The halogenation is carried out by using a halogenating agent such as pyridinum bromide, perbromide, iodine-pyridine, and lithium chloride etc. in a solvent such as ethanol-chloroform mixture, pyridine, ethyl acetate or methyl ethyl ketone, at 0° to 100° C. for 1 to 10 hours.

The Geldanamycin derivative having the formula (II) can be obtained by methylation of Geldanamycin.

Suitable methylating agents include methyl halides such as methyl chloride, methyl bromide and methyl iodide.

The methylation is carried out by dissolving Geldanamycin into an organic solvent such as chloroform, methanol or a mixture thereof and adding excess especially 4 to 6 times of silver oxide into the solution in a form of suspension and then, adding 8 to 10 times of methyl halide and mixing them. In general, the reaction is accomplished at room temperature for 3 to 24 hours.

In the reaction, several compounds having the formula (I) can be simultaneously obtained.

The Geldanamycin derivative having the formula (III) can be obtained by an epoxidation.

The compound (II) can be obtained by an epoxidation with an oxidant in an organic solvent such as chloroform, benzene, or a mixture thereof.

Suitable oxidizing agent include organic or inorganic peroxides such as peracetic acid, perbenzoic acid, chloroperbenzoic acid, perphthalic acid etc.; or alkylhalide peroxides such as t-butylhydroperoxide or hydrogen peroxide.

Excess of the oxidizing agent preferably 1.1 to 1.5 mole-equivalent per Geldanamycin can be used. When hydroperoxide is used, it is preferable to incorporate a catalytic amount of vanadium (IV) oxyacetyl acetonate. When hydrogen peroxide is used, it is preferable to react 2 mole of hydrogen peroxide with 1 mole of Geldanamycin in the presence of 4 mole of para-chlorophenyl isocyanate. The reaction is carried out at from room temperature to the boiling point of the mixture for 2 to 80 hours.

In the epoxidation of Geldanamycin by the peroxide, only double bond at 8 and 9 positions is epoxidized.

The isolation and the purification of the object compound can be carried out by conventional methods.

When the amine (IV) is used, excess of the amine is removed by washing with a dilute mineral acid. The solution is concentrated and dried at 35° to 45° C. under a reduced pressure and the residue is purified by a chromatography or a recrystallization.

The geldanamycin derivatives having the formula (I) are crystalline compounds (red, reddish violet, brown, blue) which are not soluble in water but soluble in an organic solvent such as methanol, ethanol, acetone, ethyl acetate, halogenated hydrocarbon, tetrahydrofuran, dioxane, dimethylsulfoxide, dimethylformamide and pyridine.

The Geldanamycin derivatives (I) are reduced with a reducing agent such as hydrogensulfite, dithionite, zinc-acetic acid or ascorbic acid to be pale yellow or white, but the reduced products are easily oxidized by contacting with air or an oxidizing agent to be colored and to form the Geldanamycin derivatives (I).

When the methylation is carried out to obtain the Geldanamycin derivatives having the formula (II), the isolation and the purification from the reaction mixture can be carried out by separating insoluble silver iodide and excess of silver oxide and concentrating the filtrate to dryness under a reduced pressure and purifying the residue by a chromatography or a recrystallization.

The Geldanamycin derivatives (II) are crystalline compounds (yellow or yellowish brown) which are not soluble in water but soluble in said organic solvent.

When the oxidation is carried out to obtain the Geldanamycin derivatives having the formula (III), the isolation and the purification from the reaction mixture can be carried out by separating excess of the oxidizing agent by washing with 5% aqueous solution of sodium sulfite and dehydrating the solution over anhydrous sodium sulfate and concentrating the filtrate to dryness under a reduced pressure and purifying the residue by a chromatography or a recrystallization.

The Geldanamycin derivatives (II) are crystalline compounds (yellowish brown or yellow) which are not soluble in water but soluble in said organic solvent.

The novel Geldanamycin derivatives (I), (II) or (III) of the present invention have significant growth inhibition effect to cancer cell W-2K-11 which is well-known as the model of cancer cells, to be useful as antitumor drugs.

One or more kinds of the Geldanamycin derivatives (I), (II) or (III) of the present invention can be administered as an antitumor drug.

It is preferable to combine the active ingredient with a suitable adjuvant or an additive so as to form a pharmacological composition which is suitable for oral administration or non-oral administration.

The adjuvants and additives can be the following organic or inorganic solid or liquid.

Suitable adjuvants include water, gelatin, lactose, starch, calcium, carboxymethyl cellulose, microcrystalline cellulose, stearyl alcohol, magnesium stearate, talc, vegetable oil, benzyl alcohol, propyleneglycol, rubber, polyalkyleneglycol, kerosen, jelly and cholesterol.

Suitable additives includes preservatives, wetting agents, emulsifiers, dissolution accelerators, osmotic pressure adjusting salts, buffers, binders, suspending agents and dispersing agents.

The pharmacological compositions can be powder, granule, capsule, pellet, tablet, sugar coated tablet, injection, suppository and ointment. These compositions can be prepared by conventional methods.

The antitumor drug of the present invention can be used for human therapy but also used as an animal drug, in the same form.

In the therapy with the antitumor drug of the present invention, a dose of the antitumor drug is usually in a range of 0.5 to 80 mg./kg. preferably 1 to 40 mg./kg. in the non-oral administration (injection) and in a range of 1 to 100 mg./kg. preferably 2 to 50 mg./kg. in the oral administration.

The present invention will be further illustrated by certain examples of the preparations.

EXAMPLE 1

Into 50 ml. of chloroform, 280 mg. of Geldanamycin was dissolved and then, 1 ml. of n-propylamine was added. The mixture was stirred at room temperature for 1 hour and the mixture was charged into 50 ml. of cold water and then, pH was adjusted 3 with 6 N-HCl. The chloroform layer was separated and the water layer was extructed with 50 ml. of chloroform. Both chloroform layers were combined and dehydrated over anhydrous sodium sulfate for 2 hours. Chloroform was distilled off under a reduced pressure to remain a reddish violet solid product. The solid product was recrystallized from acetone-n-hexane to obtain 286 mg. (yield 98%) of 17-n-propylamino-Geldanamycin as reddish violet acicular crystal.

Melting point: 143°–145° C.
Elementary analysis: $C_{31}H_{45}N_3O_8$.

|  | C | H | N |
| --- | --- | --- | --- |
| Calculated (%) | 63.35 | 7.72 | 7.15 |
| Found (%) | 63.35 | 7.78 | 6.96 | molecular weight (m/e): 587 (M+) (mass spectrograph).

EXAMPLE 2

Into 100 ml. of chloroform, 560 mg. of Geldanamycin was dissolved and then, 2 ml. of ethyleneimine was added. The mixture was stirred at room temperature for 21 hours and was charged into 100 ml. of cold water and pH was adjusted to 3 with 6 N-HCl. The chloroform layer was separated. The water layer was extracted with 100 ml. of chloroform. Both chloroform layers were combined and dehydrated over anhydrous sodium sulfate and concentrated to dryness under a reduced pressure to obtain a red oily product. The oily product was purified by a silica gel column chromatography with 25% methanol-chloroform. The desired fraction was collected by a fraction collector and concentrated to dryness under a reduced pressure and the product was recrystallized from acetone-n-hexane to obtain 530 mg. (yield 93%) of 17-ethyleneimino-Geldenamycin as a reddish orange crystal.

Melting point: 261°–262° C. (decomposition).
Elementary analysis: $C_{30}H_{41}N_3O_8$.

|  | C | H | N |
| --- | --- | --- | --- |
| Calculated (%) | 63.03 | 7.23 | 7.35 |
| Found (%) | 62.98 | 7.34 | 7.11 |

Molecular weight (m/e): 571 (M+) (mass spectrograph).

In accordance with the process of Example 1 or 2, the compounds shown in Table 1 were produced.

TABLE 1

| Example | Compound having formula(I) $R^1$ | Melting point(°C.) | MW. by mass spect. (m/e) |
| --- | --- | --- | --- |
| 3 | ethylamino | 226–227 | 573 |
| 4 | β-aminoethylamino | 225–227 | 588 |
| 5 | n-butylamino | 153–155 | 601 |
| 6 | n-pentylamino | 162–164 | 615 |
| 7 | n-hexylamino | 201–203 | 629 |
| 8 | n-heptylamino | 208–210 | 643 |
| 9 | n-octylamino | 215–217 | 657 |
| 10 | n-decylamino | 198–200 | 685 |
| 11 | n-dodecylamino | 207–208 | 713 |
| 12 | isobutylamino | 147–149 | 601 |
| 13 | cyclopropylamino | 210–212 | 585 |
| 14 | cyclopentylamino | 160–163 | 613 |
| 15 | cyclohexylamino | 187–189 | 627 |
| 16 | cycloheptylamino | 200–202 | 641 |
| 17 | adamanthylmethylamino | 153–155 | 693 |
| 18 | β-hydroxyethylamino | 150–152 | 589 |
| 19 | diglycolamino | 128–130 | 633 |
| 20 | β-chloroethylamino | 150–152 | 609 607 |
| 21 | δ-amino-n-butylamino | 152–155 | 616 |
| 22 | allylamino | 212–214 | 585 |
| 23 | benzylamino | 187–188 | 635 |
| 24 | phenethylamino | 185–187 | 649 |
| 25 | pyrrolidino | 150–153 | 599 |
| 26 | β-morphorimoethylamino | 167–169 | 658 |
| 27 | β-piperadinoethylamino | 188–190 | 657 |
| 28 | 2'-picolylamino | 201–203 | 636 |
| 29 | 3'-picolylamino | 235–236 | 636 |
| 30 | 4'-picolylamino | 230–231 (decomp.) | 636 |
| 31 | 2'-pyridinylethylamino | 210–211 (decomp.) | 650 |
| 32 | β-pyrrolidinoethylamino | 144–146 | 642 |
| 33 | β-methoxyethylamino | 128–130 | 603 |
| 34 | β-N-methylethylamino | 152–155 (decomp.) | 602 |

EXAMPLE 35

Into 100 ml. of chloroform-methanol (3:2), 560 mg. of Geldanamycin was dissolved and then, 30 ml. of 50% aqueous solution of dimethylamine was added. The mixture was stirred at room temperature for 2 hours and was charged into 100 ml. of cold water and pH was adjusted to 3 to 4 with 6N-HCl. The product was extracted twice with chloroform and the extracted chloroform layers were washed with water and dehydrated over anhydrous sodium sulfate and concentrated to dryness under a reduced pressure to obtain a blue oily product.

The oily product was purified by a silica gel column chromatography with 2% methanol-chloroform. The fractions (14th to 32th) were collected and the solvent was distilled off and the product was recrystallized from ether to obtain 52 mg. of 17-demethoxy-17,19-bis-dimethylamino-Geldenamycin as brown crystal.

Melting point: 135°–137° C.

Elementary analysis: $C_{32}H_{50}N_4O_8$.

|  | C | H | N |
|---|---|---|---|
| Calculated (%) | 62.11 | 8.15 | 9.05 |
| Found (%) | 62.01 | 8.00 | 8.87 |

NMR spectrum (100 MHz: (DCl$_3$).

δ(ppm): 2.92 (dimethylamino); 2.93 (dimethylamino); 3.31 (methoxy); 3.34 (methoxy).

UV spectrum: $\lambda_{max}^{CH3OH}$ (nm): 246, 380, 540.

Molecular weight (m/e): 618 (M+) (mass spectrograph).

EXAMPLE 36

The blue oily product obtained by the process of Example 35 was purified by a silica gel column chromatography with 2% methanol-chloroform. The fractions (34th to 70th) were collected and the solvent was distilled off and the product was recrystallized from ether-n-hexane to obtain 317 mg. of 19-dimethylamino-Geldanamycin as blue crystal.

Melting point: 153°–156° C.

Elementary analysis: $C_{31}H_{45}N_3O_9$.

|  | C | H | N |
|---|---|---|---|
| Calculated (%) | 61.67 | 7.51 | 6.96 |
| Found (%) | 61.81 | 7.98 | 6.88 |

NMR spectrum (100 MHz-CDCl$_3$).

δ(ppm): 3.00 (dimethylamino), 3.26 (methoxy), 3.33 (methoxy), 3.88 (methoxy).

UV spectrum: $\lambda_{max}^{CH3OH}$ (nm): 244, 295, 535.

Molecular weight (m/e): 603 (M+) (mass spectrograph).

EXAMPLE 37

Into 60 ml. of ethanol and 60 ml. of chloroform, 1.12 g. of Geldanamycin was dissolved. The mixture was stirred while cooling with ice water and 960 mg. of pyridinium bromide perbromide was added. The mixture was stirred further for 1 hour. After the reaction, it was diluted with large amount of chloroform and repeatedly washed with chloroform and with saturated aqueous solution of sodium chloride and dehydrated over anhydrous sodium sulfate. The chloroform layer was concentrated to dryness under a reduced pressure to obtain yellowish orange oily product. The oily product was purified by a silica gel column chromatography with 3% methanolchloroform and then, recrystallized from ethyl ether to obtain 630 mg. of 19-bromo-Geldanamycin as orange crystal.

Melting point: 224°–226° C. (decomposed).

Elementary analysis: $C_{29}H_{39}N_2O_9Br \cdot \frac{1}{2}(C_2H_5)_2O$.

|  | C | H | N | Br |
|---|---|---|---|---|
| Calculated (%) | 55.03 | 6.55 | 4.14 | 11.81 |
| Found (%) | 55.24 | 6.85 | 3.92 | 11.62 |

IR spectrum (KBr): 1747, 1684, 1590$^{cm-1}$.

UV spectrum: $\lambda_{max}^{CH3OH}$ (nm): 257, 312, 390 (sh).

Molecular weight (m/e): 640 and 638 (M+) (mass spectrograph).

EXAMPLE 38

Into 20 ml. of pyridine, 762 mg. of iodine was dissolved and 1.12 g. of Geldanamycin was dissolved. The mixture was stirred at room temperature for 1 hour. The reaction mixture was diluted with ethyl acetate. The diluted solution was washed with 5% aqueous solution of sodium thiosulfate, with 10% aqueous solution of acetic acid and with saturated aqueous solution of sodium chloride and then dehydrated over anhydrous sodium sulfate. The ethyl acetate solution was concentrated to dryness under a reduced pressure to obtain an orange red oily product. The oily product was purified by a silica gel column chromatography with 3% methanol-chloroform and recrystallized from chloroform-n-hexane to obtain 988 mg. of 19-iodo-Geldanamycin as orange crystal.

Melting point: 152°–154° C.

Elementary analysis: $C_{29}H_{39}N_2O_9I \cdot CHCl_3$.

|  | C | H | N | halogen |
|---|---|---|---|---|
| Calculated (%) | 44.71 | 5.00 | 3.48 | 27.94 |
| Found (%) | 45.16 | 5.03 | 3.47 | 27.68 |

IR spectrum (KBr); 1740, 1673, 1580$^{cm-1}$.

UV spectrum: $\lambda_{max}^{CH3OH}$ (nm): 255, 312, 405 (sh).

Molecular weight (m/e): 686 (M+) (mass spectrograph).

EXAMPLE 39

Into 60 ml. of methyl ethyl ketone, 726 mg. of 19-bromo-Geldanamycin was dissolved and 3.5 g. of lithium chloride was added. The mixture was refluxed for 5 hours with stirring. After the reaction, the reaction mixture was cooled to room temperature and diluted with a large amount of chloroform and washed with 5% aqueous solution of sodium thiosulfate, with water, with saturated aqueous solution of sodium chloride and dehydrated over anhydrous sodium sulfate. The chloroform solution was concentrated to dryness to obtain orange oily product. The oily product was purified by a silica gel column chromatography with 3% methanol-chloroform and recrystallized from chloroform-n-hexane to obtain 580 mg. of 19-chloro-Geldanamycin as reddish orange crystal.

Melting point: 157°–159° C.

Elementary analysis: $C_{29}H_{39}N_2O_9Cl \cdot CHCl_3 \cdot \frac{1}{2}H_2O$.

|  | C | H | N | Cl |
|---|---|---|---|---|
| Calculated (%) | 49.80 | 5.71 | 3.87 | 19.60 |
| Found (%) | 49.74 | 5.60 | 3.77 | 20.67 |

IR spectrum (KBr): 1730, 1680, 1588$^{cm-1}$.

UV spectrum: $\lambda_{max}^{CH3OH}$ (nm); 257, 310, 395 (sh).

Molecular weight (m/e): 596 and 594 (M+) (mass spectrograph).

EXAMPLE 40

Into 200 ml. of chloroform and 200 ml. of methanol, 5 g. of Geldanamycin was dissolved and then, 20 g. of silver oxide was added and then 40 g. of methyl iodide was added with stirring and the mixture was stirred for 5 hours. The insoluble materials were separated by a filtration and the filtrate was concentrated to dryness under a reduced pressure at 40° C. The resulting reddish orange oily product was purified by a silica gel column chromatography with 2.5% methanol-chloroform. The fractions (42th to 60th) were collected and concentrated to dryness and recrystallized from ether-n-hexane to obtain 600 mg. of 1-O-methyl-Geldanamycin as yellowish orange crystal.

Melting point: 213°–215° C.
Elementary analysis: $C_{30}H_{42}N_2O_9 \cdot \frac{1}{2}H_2O$.

|  | C | H | N |
|---|---|---|---|
| Calculated (%) | 61.73 | 7.42 | 4.80 |
| Found (%) | 62.09 | 7.37 | 4.73 |

NMR spectrum: (100 MHz: CDCl$_3$).
δ(ppm): 3.85 (iminomethyl ether).
UV spectrum: $\lambda_{max}^{CH3OH}$ (nm): 262, 305, 390 (sh).
Molecular weight (m/e): 574 (M+).

EXAMPLE 41

The fractions (77th to 128th) obtained by the silica gel column chromatography in the process of Example 40 were collected and concentrated to dryness and the product was recrystallized from chloroform-n-hexane to obtain 2.42 g. of 21-N-methyl-Geldanamycin as yellow crystal.

Melting point: 141°–143° C.
Elementary analysis: $C_{30}H_{42}N_2O_9 \cdot \frac{1}{2}H_2O$.

|  | C | H | N |
|---|---|---|---|
| Calculated (%) | 61.73 | 7.42 | 4.80 |
| Found (%) | 61.39 | 7.28 | 4.80 |

NMR spectrum: (100 MHz: CDCl$_3$).
δ(ppm): 3.12 (N-methyl).
UV spectrum: $\lambda_{max}^{CH3OH}$ (nm): 254, 316, 390 (sh).
Molecular weight (m/e): 574 (M+) (mass spectrograph).

EXAMPLE 42

The fractions (13th to 34th) obtained by the silica gel column chromatography in the process of Example 40 were collected and concentrated to dryness and the product was purified by a chromatography with 2% methanol-chloroform and recrystallized from chloroform-n-hexane to obtain 452 mg. of 21-N-methyl-7-OCONH-methyl-Geldanamycin as yellow crystal.

Melting point: 130°–132° C.
Elementary analysis: $C_{31}H_{44}N_2O_9$.

|  | C | H | N |
|---|---|---|---|
| Calculated (%) | 63.25 | 7.53 | 4.77 |
| Found (%) | 63.01 | 7.48 | 4.83 |

NMR spectrum (100 MHz: CDCl$_3$).
δ(ppm): 3.12 (N-methyl), 2.77 (N-methyl-carbamate).
UV spectrum: $\lambda_{max}^{CH3OH}$ (nm): 252, 310, 410 (sh).
Molecular weight (m/e): 588 (M+) (mass spectrograph).

EXAMPLE 43

The fractions (3rd to 12th) obtained by the silica gel column chromatography in the process of Example 40 were collected and concentrated to dryness and the product was purified by a chromatography with % methanol-chloroform to collect the fractions (1st to 40th) and the fraction was crystallized from acetone-n-hexane to obtain 192 mg. of 7-OCONH-methyl Geldanamycin as yellow acicular crystal.

Melting point: 230°–232° C.
Elementary analysis: $C_{30}H_{42}N_2O_9 \cdot \frac{1}{2}H_2O$.

|  | C | H | N |
|---|---|---|---|
| Calculated (%) | 61.73 | 7.42 | 4.80 |
| Found (%) | 62.01 | 7.35 | 4.73 |

NMR spectrum: (100 MHz: CDCl$_3$).
δ(ppm): 2.80 (N-methyl carbamate), 8.75 (N-H).
UV spectrum: $\lambda_{max}^{CH3OH}$ (nm): 258, 303, 404.
Molecular weight (m/e): 574 (M+) (mass spectrograph).

EXAMPLE 44

The fractions (61st to 82nd) obtained by the second gel column chromatography in the process of Example 43 were collected and recrystallized from chloroform-n-hexane to obtain 343 mg. of 1-O-methyl-7-OCONH-methyl-Geldanamycin as yellow crystal.

Melting point: 119°–121° C.
Elementary analysis: $C_{31}H_{44}N_2O_9 \cdot H_2O$.

|  | C | H | N |
|---|---|---|---|
| Calculated (%) | 61.36 | 7.64 | 4.62 |
| Found (%) | 61.10 | 7.58 | 4.50 |

NMR spectrum: (100 MHz; CDCl$_3$).
δ(ppm): 2.75 (N-methyl-carbamate), 3.85 (iminomethyl ether).
UV spectrum: $\lambda_{max}^{CH3OH}$ (nm): 263, 295 (sh), 410 (sh).
Molecular weight (m/e): 588 (M+) (mass spectrograph).

EXAMPLE 45

Into 800 ml. of 20 % benzene-chloroform, 5.6 g. of Geldanamycin was dissolved and then, 1.9 g. of methachlorobenzoic acid was added. The mixture was stirred at room temperature for 5 hours. The reaction mixture was washed with 5% aqueous solution of sodium sulfite and with water and with saturated aqueous solution of sodium chloride and dehydrated over anhydrous sodium sulfate and concentrated to dryness under a reduced pressure. The resulting orange red oily reside was purified by a silica gel column chromatography with 3%-methanol-chloroform. The desired fractions were collected and concentrated to dryness under a reduced pressure and recrystallized from ether-n-hexane to obtain 4.84 g. of 8,9-epoxy-Geldanamycin as yellowish orange crystal.

Melting point: 148°–149° C.
Elementary analysis: $C_{29}H_{40}N_2O_{10} \cdot \frac{1}{2}H_2O$.

|  | C | H | N |
|---|---|---|---|
| Calculated (%) | 59.47 | 7.06 | 4.78 |
| Found (%) | 59.54 | 6.96 | 4.71 |

UV spectrum: $\lambda_{max}^{CH3OH}$ (nm): 254, 303, 407.
Molecular weight (m/e): 576 (M+) (mass spectrograph).

EXAMPLE 46

Into 1000 ml. of benzene, 1.4 g. of Geldanamycin was dissolved and a catalytic amount of vanadium (IV) oxyacetyl acetonate was added and the mixture was refluxed on an oil bath and 360 mg. of 70% t-butylhydroperoxide was added during the reflux. After refluxing for 6 hours, the reaction mixture was cooled to room temperature and was washed with 0.1N-HCl, with 5% aqueous solution of sodium sulfite, with water and with saturated aqueous solution of sodium chloride and dehydrated over anhydrous sodium sulfate and concentrated to dryness under reduced pressure. The resulting residue was purified by a silica gel column chromatography with 2.5% methanol-chloroform. The desired fractions were collected and concentrated to dryness and recrystallized from ether to obtain 280 mg. of 8,9-epoxy-Geldanamycin as yellowish orange crystal.

According to the silica gel thin layer chromatography, the melting point and the IR spectrum, it was confirmed that the product was the same as the product of Example 45.

Composition

2500 G. of each product, 1375 g. of lactose, 775 g. of microcrystalline cellulose and 375 g. of calcium carboxymethyl-cellulose were sieved by a 16 mesh sieve to mix uniformly them. The mixture was charged into a kneader and 3 liter of 3% solution of hydroxypropyl-cellulose (isopropyl alcohol:water=3:7), was added and the mixture was kneaded. The mixture was granulated by an extrusion-granulating machine and air-dired at 50° C. for 6 hours. The granule was dressed in a range of 16 to 60 mesh and magnesium stearate was admixed with the granule at a ratio of 0.3 wt. % and the mixture was tabletted to obtain tablet.

Test

Cancer cell W-2K-11 was obtained by transforming fibroblast C3H-2K clone derived from kidney of mouse by cancerogenic virus. The cancer cell W-2K-11 was cultured by the following method.

(1) Preparation of culture medium 9.4 Gram of Eagle's MEM culture media (manufactured by Nissui Seiyaku K. K.) was dissolved in 900 ml. of distilled water and the solution was sterilized under high pressure at 120° C. for 15 minutes and cooled. 100 Ml. of calf serum and 3–5 ml. of 10% aqueous solution of sodium bicarbonate were added to the solution to adjust pH to 7.1–7.2. 10 Ml. of an aqueous solution of L-glutamine (2.92 g./100 ml.) filtered by a millipore filter was added just before the use of the solution as culture medium.

(2) Preparation of transplanted cell solution

The cancer cell W-2K-11 stored in a freezer at $-80°$ C. was melted at room temperature and treated by a centrifugal separator at 670 g. for 5 minutes. The precipitated cell was dispersed in 50 ml. of the culture medium (1). The suspension was charged into Roux flask and cultured at 37° C. The multiplication of the cells was initiated and accomplished after 3 to 4 days. The cultured mixture was decanted and 10 ml. of 0.2% trypsin solution was added and the mixture was kept at room temperature for 2 to 3 minutes and the trypsin mixture was decanted and then, 50 ml. of the culture medium (1) was added to prepare a suspension of cells.

(3) Incubation of cells and addition of sample 1.8 Ml. of the suspension of cells (2) was charged into each Petri dish and incubated in a carbon dioxide gas incubator (5% of $CO_2$; 95% of air) at 37° C. Twenty four hours after the initiation of the incubation, 0.2 ml. of each ethanol solution of each sample was added, and the incubation was continued. Forty eight hours after the addition of the sample, numbers of survival cells were counted under a microscopic observation and each percent inhibition of cell multiplication was calculated. The results are shown in Table 2.

$$\text{Percent inhibition (\%)} = \frac{\left(\begin{array}{c}\text{Number of cells}\\\text{in Petri dish}\\\text{(no addition)}\end{array}\right) - \left(\begin{array}{c}\text{Number of cells}\\\text{in Petri dish}\\\text{(addition)}\end{array}\right)}{\left(\begin{array}{c}\text{Number of cells in}\\\text{Petri dish (no addition)}\end{array}\right)} \times 100$$

TABLE 2

| Compound No. (Example No.) | Concentration (μg/ml.) | Percent inhibition (%) |
|---|---|---|
| 1 | 1 | 92 |
| 2 | 1 | 97 |
| 3 | 1 | 90 |
| 4 | 5 | 57 |
| 5 | 1 | 85 |
| 6 | 1 | 90 |
| 7 | 1 | 90 |
| 8 | 1 | 96 |
| 9 | 10 | 67 |
| 10 | 10 | 48 |
| 11 | 10 | 79 |
| 12 | 1 | 90 |
| 13 | 1 | 94 |
| 14 | 1 | 98 |
| 14 | 10 | 97 |
| 15 | 1 | 98 |
| 16 | 10 | 98 |
| 17 | 10 | 98 |
| 18 | 1 | 98 |
| 19 | 10 | 88 |
| 20 | 1 | 98 |
| 21 | 10 | 53 |
| 22 | 1 | 93 |
| 23 | 1 | 88 |
| 24 | 1 | 82 |
| 25 | 10 | 97 |
| 26 | 5 | 93 |
| 27 | 5 | 57 |
| 28 | 5 | 90 |
| 29 | 5 | 92 |
| 30 | 5 | 95 |
| 31 | 5 | 93 |
| 32 | 5 | 84 |
| 33 | 0.5 | 95 |
| 34 | 5 | 67 |
| 35 | 10 | 97 |
| 35 | 1 | 92 |
| 36 | 10 | 84 |
| 36 | 1 | 70 |
| 37 | 5 | 84 |
| 38 | 5 | 95 |
| 39 | 5 | 91 |
| 40 | 10 | 95 |
| 40 | 1 | 80 |
| 41 | 10 | 82 |
| 42 | 10 | 94 |
| 42 | 1 | 82 |
| 43 | 10 | 96 |
| 43 | 1 | 60 |
| 44 | 10 | 80 |
| 44 | 1 | 94 |
| 45 | 10 | 100 |
| 45 | 1 | 95 |
| Geldanamycin | 1.2 | 61 |

Acute toxicity $LD_{50}$ of each sample to mouse was measured by intraperitoneal injection of each sample. The results are shown in Table 3.

TABLE 3

| Compound No. (Example No.) | $LD_{50}$ |
|---|---|
| 3 | 120 mg./kg. |
| 36 | >240 mg./kg. |
| 41 | 120 mg./kg. |
| 45 | 240 mg./kg. |
| Geldanamycin | 15 mg./kg. |

We claim:
1. A geldanamycin having the following formula:

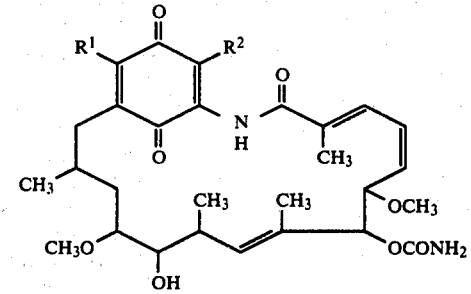

(I)

wherein $R^1$ represents
(A)

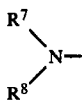

wherein $R^7$ and $R^8$ respectively represent hydrogen; alkyl of 2-12 carbon atoms; alkyl of 2-12 carbon atoms substituted with hydroxy, amino, methylamino, pyrrolidino, pyridinyl, methoxy, piperidino, morpholino, glycoxy or halogen; cycloalkyl of 3-8 carbon atoms; adamanthyl; benzyl; phenethyl; picolyl; allyl; or diglycol; with the proviso that both $R^7$ and $R^8$ can be bonded to form one alkylene group of 2-6 carbon atoms; or
(B) methoxy;
wherein $R^2$ represents hydrogen, halogen, or an alkylamino group wherein the alkyl group has 2-12 carbon atoms; with the proviso that when $R^1$ is methoxy, $R^2$ is halogen or an alkylamino group wherein the alkyl group has 2-12 carbon atoms;
or

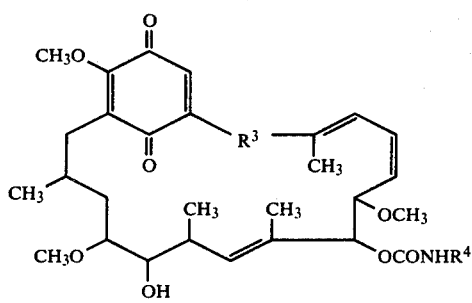

(II)

wherein $R^3$ represents

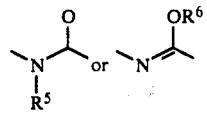

$R^4$, $R^5$ & $R^6$ respectively represent hydrogen atom or methyl group and at least one of $R^4$, $R^5$ and $R^6$ is a methyl group;
or

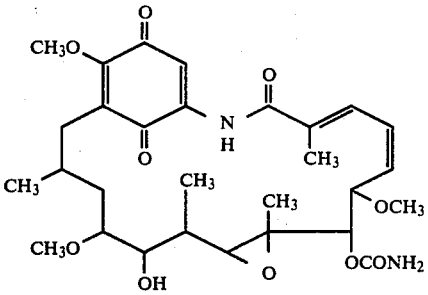

(III)

2. A geldanamycin having the following formula:

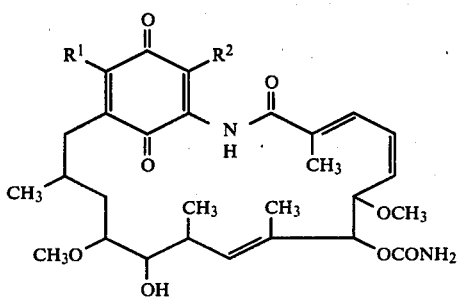

(I)

wherein $R^1$ represents
(A)

wherein $R^7$ and $R^8$ respectively represent hydrogen; alkyl of 2-12 carbon atoms; alkyl of 2-12 carbon atoms substituted with hydroxy, amino, methylamino, pyrrolidino, pyridinyl, methoxy, piperidino, morpholino, glycoxy or halogen; cycloalkyl of 3-8 carbon atoms; adamanthyl; benzyl; phenethyl; picolyl; allyl; or diglycol; with the proviso that both $R^7$ and $R^8$ can not be hydrogen; and $R^7$ and $R^8$ can be bonded to form one alkylene group of 2-6 carbon atoms; or
(B) methoxy;
wherein $R^2$ represents hydrogen, halogen, or an alkylamino group wherein the alkyl group has 2-12 carbon atoms; with the proviso that when $R^1$ is methoxy, $R^2$ is halogen or an alkylamino group wherein the alkyl group has 2-12 carbon atoms.

3. The geldanamycin of claim 2, wherein $R^1$ is a methoxy group and $R^2$ is a halogen atom or an alkylamino group wherein the alkyl group has 2-12 carbon atoms.

4. A geldanamycin having the formula

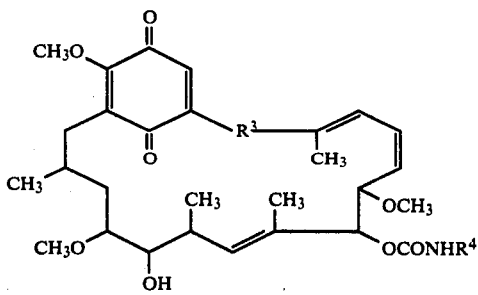

wherein $R^3$ represents

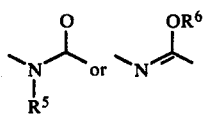

$R^4$, $R^5$ and $R^6$ respectively represent hydrogen atom or methyl group and at least one of $R^4$, $R^5$ and $R^6$ is methyl group.

5. A geldanamycin having the formula

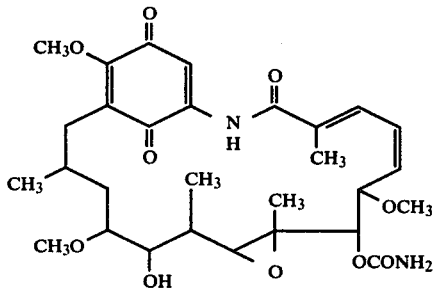

6. A process for producing the geldanamycin of claim 1 having the formula (I) which comprises reacting Geldanamycin with an amine having the formula

wherein $R^7$ and $R^8$ respectively represent hydrogen; alkyl of 2-12 carbon atoms; alkyl of 2-12 carbon atoms substituted with hydroxy, amino, methylamino, pyrrolidino, pyridinyl, methoxy, piperidino, morpholino, glycoxy, or halogen; cycloalkyl of 3-8 carbon atoms; adamanthyl; benzyl; phenethyl; picolyl; allyl; or diglycol; with the proviso that both $R^7$ and $R^8$ can not be hydrogen; and $R^7$ and $R^8$ can be bonded to form one alkylene group of 2-6 carbon atoms.

7. The process of claim 6, wehrein said amine is ethylamine, propylamine, butylamine, pentylamine, hexylamine, heptylamine, octylamine, decylamine, dodecylamine, allylamine, β-hydroxyethylamine, β-chloroethylamine, β-glycoxyethylamine, aminobutylamine, adamanthylmethylamine, cyclopropylamine, cyclopentylamine, cyclohexylamine, cycloheptylamine, benzylamine, phenethylamine, ethyleneimine, pyrrolidine, piperidine, dimethylamine, aminoethylamine, β-hydroxyethylamine, diglycolamine, β-morpholinoethylamine, β-piperadinoethylamine, 2'-, or 3'-, or 4'-picolylamine, β-pyrrolidinoethylamine, 2'-pyridinylethylamine, β-methoxyethylamine or β-N-methylaminoethylamine.

8. The process of claim 6 wherein the reaction of Geldanamycin with the amine is carried out in the presence of an organic solvent.

9. The process of claim 6, wherein an excess of alkylamine is used in the reaction, so that both $R^1$ and $R^2$ are partially converted into the corresponding alkylamino groups, though $R^1$ is partially retained as methoxy group.

10. A process for producing the geldanamycin of claim 1 having the formula (I) wherein $R^1$ is methoxy and $R^2$ is halogen comprising the halogenation of Geldanamycin.

11. A process for producing the geldanamycin of claim 1 having the formula (II) comprising the methylation of Geldanamycin.

12. The process of claim 11, wherein the methylating agent is methyl halide.

13. A process for producing the geldanamycin of claim 1 having the formula (III) comprising the epoxidation of Geldanamycin.

14. An antitumor composition which comprises an antitumor effective amount of the geldanamycin of claim 1 and a pharmacologically acceptable adjuvant or additive.

* * * * *

UNITED STATES PATENT AND TRADEMARK OFFICE
CERTIFICATE OF CORRECTION

PATENT NO. : 4,261,989

DATED : April 14, 1981

INVENTOR(S) : Kazuya Sasaki et al

It is certified that error appears in the above—identified patent and that said Letters Patent is hereby corrected as shown below:

Front page, left hand column, in between sections [22] and [51], [30] add

February 19, 1979 Japan 17219/1979
February 20, 1979 Japan 17868/1979
February 27, 1979 Japan 21380/1979

Signed and Sealed this

Twenty-sixth Day of July 1983.

[SEAL]

Attest:

Attesting Officer

GERALD J. MOSSINGHOFF

Commissioner of Patents and Trademarks